United States Patent [19]
Lipps et al.

[11] Patent Number: 5,744,449
[45] Date of Patent: *Apr. 28, 1998

[54] LETHAL TOXIN NEUTRALIZING FACTORS

[76] Inventors: Binie V. Lipps; Frederick W. Lipps, both of 4509 Mimosa Dr., Bellaire, Tex. 77401

[ * ] Notice: The term of this patent shall not extend beyond the expiration date of Pat. No. 5,576,297.

[21] Appl. No.: 657,163

[22] Filed: Jun. 3, 1996

Related U.S. Application Data

[63] Continuation-in-part of Ser. No. 310,340, Sep. 22, 1994, Pat. No. 5,576,297, which is a continuation-in-part of Ser. No. 58,387, May 10, 1993, abandoned.

[51] Int. Cl.[6] .......................... A61K 38/10; A61K 38/16; C07K 7/08; C07K 14/47

[52] U.S. Cl. .................................. 514/14; 514/8; 514/12; 514/21; 530/300; 530/326; 530/350; 530/362; 530/380; 530/416; 530/829; 530/830

[58] Field of Search .................................. 514/8, 12, 21, 514/14; 530/350, 300, 326, 362, 363, 364, 380, 412, 416, 829, 830, 856

[56] References Cited

U.S. PATENT DOCUMENTS 5,576,297 11/1996 Lipps et al. .............................. 514/14

OTHER PUBLICATIONS

Bone "The Pathogenesis of Sepsis" Ann Int Med. 115(6) 457–469, 1991.

Guyton "Textbook of Medical Physiology" 8th Ed. 269–271, 1991.

Mousstaché et al. "Mechanisms of Resistance of the Opossum to Some Snake Venoms" Toxicon 17(Suppl. 1) 130, 1979.

Perales et al. "Neutralization of the Oedematogenic activity of Bothrops Jararaca venom on the Mouse Paw . . . " Agents & Actions 37(3–4) 250–259, 1992.

Tomihara et al. "Purification of Three Antihemorrhagic Factors From the Serum of a Mongoose" Toxicon 25(6) 685–689, 1987.

Perates et al "Anti Snake Venom Protein from Didelphidae" Abstract 10th World Congress Toxicon 30(5–6) 543, 1992.

Menchaca et al. "The Purification & Characterization of an Antihemerrhagic Factor in Opossum Serum" Toxicon 19(5) 623–632, 1981.

Domont et al. "Natural Anti–Snake Venom Proteins" Toxicon 29(10) 1183–1194, 1991.

*Primary Examiner*—Nancy Degen
*Attorney, Agent, or Firm*—John R Casperson

[57] ABSTRACT

Opossum whole serum exhibits a life saving property by neutralizing the lethality of venoms from all major families of poisonous snakes, and therefore an injection of Opossum serum can used as a novel treatment for many types of envenomation. Preferably, the injectable treatment for envenomation should be a composition obtained from the fraction of Opossum whole serum which contains the LTNF, i. e. the so called "LTNF-n", in purity. A method is given for the manufacture of a LTNF from the serum of an opossum (*Didelphis virginiana*) serum, by fractionating the opossum serum and isolating this select fraction from the plurality of fractions having an N terminal amino acid sequence given by SEQ ID No: 1. A short peptide was synthesized having SEQ ID No: 1. The synthetic peptide having the sequence SEQ ID No: 1 shows lethal toxin neutralizing activity similar to the natural LTNF from opossum or mongoose sera. The synthetic LTNF also has life saving utility.

20 Claims, 3 Drawing Sheets

LETHAL TOXIN NEUTRALIZING FACTORS

This application is a continuation in part of application Ser. No. 08/310,340, filed Sep. 22, 1994, now U.S. Pat. No. 5,576,297, which was a continuation in part of the application Ser. No. 08/058,387, filed May 10, 1993, now abandoned.

BACKGROUND OF THE INVENTION

The present invention embodies a treatment for diverse envenomation and intoxication which can be used in life saving applications. More particularly, the present invention relates to a molecular moiety called "lethal toxin neutralizing factor", hereinafter "LTNF", for the treatment of venomous snake bites and other types of envenomation, toxicities and disorders.

Currently, antivenoms produced in horses provide the only available treatment for snakebite, in spite of the fact that some people are hypersensitive to horse proteins. Antivenom treatment for snakebite has been in practice for over forty years without much improvement. The only consideration being, that antivenoms for snake species prevalent to the region be available, and that the correct antivenom should be used. In order to administer the proper specific antivenom, the victim or physician must identify the guilty snake, which is impossible in many cases. Numerous antivenoms now exist worldwide, which are mostly made in horse, although a few are made in goats. It would be desirable to find combinations of venoms giving a broad spectrum of protective antibodies, but this has not yet happened.

Treatment of snakebite would be greatly enhanced, if a drug could be found which would overcome the problems associated with antivenoms. A drug which will neutralize the toxicity of venoms from all major species will be a breakthrough.

Several warm-blooded animals, such as opossums, mongoose, meerkats, wood rats and cotton rats have shown a remarkable resistance to the toxic action of snake venoms. An antihemorrhagic factor in serum of *Sigmodon hispidus* (cotton rat), has been isolated and characterized. This antihemorrhagic factor has physical properties different from the immunoglobulins of serum. An antihemorrhagic factor has also been isolated, purified and characterized from opossum serum. The opossum serum derived antihemorrhagic factor has an isoelectric pH 4.1 and molecular weight 68,000 daltons. According to the art of the published work, the antihemorrhagic factor in the serum of opossum is albumin or closely associated with albumin. However, these investigators did not claim the utility of antihemorrhagic factor as a treatment for snakebite, nor did they measure its neutralizing activity versus venom toxins except for observing its effect on skin hemorrhage.

OBJECTS OF THE INVENTION

It is an object of the present invention to provide a composition consisting of a natural LTNF (LTNF-n) derived from opossum serum that serves as a relatively universal treatment for snakebite. Said LTNF is an effective life saving treatment for snakebite for a large variety of snakes having diverse type of lethal activities. It is a further object of the present invention to provide a LTNF that does not include horse proteins.

It is also an object of the present invention to provide a short synthetic peptide (LTNF-s) utilizing a portion of the LTNF-n molecule which also has activity as a lethal toxin neutralizing factor with the same or similar utility as the naturally occurring product.

It is a further object of this invention to use both natural (LTNF-n) and synthetic LTNF (LTNF-s) to treat sepsis, allergies etc. and other nonspecific disorders caused by environment, as well as for treatment of bee stings, scorpion stings or toxicities caused by plant or bacterial toxins.

Thus, both embodiments of the present invention, i. e. LTNF-n and LTNF-s, can become alternative treatments for various snakebites as well as for treatment of exposures which may occur under military conditions of chemical or biological warfare and/or for other toxicities such as those resulting from scorpion and bee stings, and also toxins from plants such as Ricin, bacteria such as botulism, etc.

Both LTNF-n and LTNF-s can be given intravenously for the treatment of snakebite in a manner similar to an antivenom treatment to give a systemic effect rather than given topically or by perfusing the bite-wound to give a localized effect such as antihemorrhage. For treatment of localized inflammation, the LTNF can be administered topically. For universal application, it is expected that LTNF-s can also be administered orally or by nasal insufflation and provide good results.

TERMINOLOGY

As used herein, LTNF-n refers to natural LTNF isolated from opossum serum having a molecular weight of about 68 kDa and the first 15 amino acids from the N-terminal as identified in Sequence ID No. 1.

Synthetic LTNF or LTNF-s refers to a synthetic peptide having a molecular weight of less than 2,500 and at least a portion of the sequence set forth in Sequence ID No. 1. Preferably, LTNF-s has at least a 3-amino acid portion of the sequence, more preferably, at least a 5 amino acid portion of the sequence, and most preferably, at least a 7 amino acid portion of the sequence. Specific examples of LTNF-s include LTNF-15, LTNF-10 and LTNF-5. LTNF-15 is the 15 amino acid peptide having the sequence from the N-terminal set forth in Sequence ID No. 1 and a molecular weight of about 1,989. LTNF-15 has been tested with good results. LTNF-10 is the 10 amino acid peptide having the sequence from the N-terminal set forth in Sequence ID No. 2 and has been tested with good results. LTNF-5 is the 5 amino acid peptide having the sequence from the N-terminal set forth in Sequence ID No. 3. While LTNF-5 has not been tested, it is expected to be active because the 5 amino acid sequence is found in several species of animals known to be resistant to envenomation. Based on this, it is believed likely that LTNF-s requires an at least 3 amino acid sequence, preferably an at least 5 amino acid sequence, and most preferably, an at least 7 amino acid sequence, from the N-terminal of the sequence set forth in Sequence ID No. 1. The molecular weight of LTNF-s will generally be in the 250–2500 range and usually in the 500–2,000 range.

SUMMARY OF THE INVENTION

This invention relates to: (1) the lethal toxin neutralizing effect of opossum serum; (2) a purified component from opossum serum having lethal toxin neutralizing activity; and (3) a family of synthetic peptides having similar lethal toxin neutralizing activity for crude venoms of various species of snakes containing diverse deadly toxins acting in different physiological ways. All three: opossum serum; the purified fraction from opossum serum; and the synthetic peptides provide relatively universal treatment for snakebite. All three neutralize venoms from the major families of poisonous snakes, and therefore, provide a replacement for antivenoms made in horses.

The present invention is a method of producing LTNF-n and LTNF-s having utility as a life saving agent for use with diverse venoms and toxins. The naturally occurring factor requires: (1) obtaining opossum serum; (2) fractionating the opossum serum into a plurality of fractions; (3) identifying and isolating the fraction having the lethal toxin neutralizing activity for venoms from the major families of poisonous snakes. The synthetic factor requires synthesizing a short peptide of fifteen or fewer amino acids from the first 15 N terminal amino acids of the naturally occurring factor from opossum serum. The LTNF-15 and the first 15 N-terminal amino acids of the naturally occurring factor have the sequence: Leu-Lys-Ala-Met-Asp-Pro-Thr-Pro-Pro-Leu-Trp-Ile-Lys-Thr-Glu, which will be referred to as SEQ ID No: 1.

The purification of the naturally occurring LTNF includes fractionating the opossum serum on an anion exchange column of a liquid phase fractionating system. This liquid phase fractionating system is a high pressure liquid chromatography system. The fractions of the opossum serum are eluted with a buffer material. This buffer material is an aqueous gradient Trizma-HCl buffer having the Ph 7.4 and molarity in the gradient range of 0.01 molar to 1.0 molar.

The eluted fractions of opossum serum are dialyzed against distilled water as to remove the buffer chemicals. Initially, all fractions were tested for the lethal toxin neutralizing activity and the one fraction having such activity is called the natural lethal toxin neutralizing factor, "LTNF-n". This is a reproducible procedure and the same fraction always has the lethal toxin neutralizing activity for various venoms.

Lethality of venom can be due to several types of toxins present in the venom which exert different physiological effects, such as respiratory failure, blood clotting, muscular paralysis, cardiac arrest, cell lysis and hemorrhage; whereas, hemorrhage is only one of many causes of death due to envenomation. The LTNF exhibits the ability to neutralize all effects associated with the lethality of snake venom toxins in mice. The LTNF of the present invention shows inhibition or neutralization of toxins from the venoms of major families of snakes.

The LTNF-15 shows similar neutralization activity for toxins from venoms when tested in mice. An extremely low concentration of this LTNF is required to neutralize the lethal effect of snake venoms in comparison to the protein concentration required using currently available antivenom. On a weight basis, LTNF-10 is even more efficacious than LTNF-15. Thus, both compositions of the present invention, LTNF-n and LTNF-s can become alternative treatments for various snakebites and it is believed that their use can be extended to treat scorpion and bee stings, including toxins from plants, bacteria, etc.

BRIEF DESCRIPTION OF THE DRAWINGS

Drawing No. 1: High pressure liquid chromatography profile of opossum serum, using anion exchange column. Peak number six represents the natural LTNF-n derived from opossum serum.

Drawing No. 2: High pressure liquid chromatography profile of concentrate from fraction number six showing single peak of pure LTNF-n.

Drawing No. 3: Electrophoretic profile of opossum serum and purified LTNF-n on 14% Novex gel with markers. The molecular weight of LTNF-n corresponds to the albumin component of the opossum serum and the marker bovine serum albumin, which is approximately 68,000 daltons. Well no. 1: LTNF-15; Well no. 2 LTNF-n; Well no. 3: Opossum Serum; Well no. 4: Markers.

DETAILED DESCRIPTION OF THE INVENTION

Whole sera from opossum and mongoose were tested for their neutralizing property versus several snake venoms belonging to four major families of poisonous snakes: Crotalidae, Elapidae Hydrolidae and Viperidae. The following sample of venoms were tested:

| | |
|---|---|
| Crotalus adamanteus | Family Crotalidae |
| Crotalus atrox | Family Crotalidae |
| Naja n. atra | Family Elapidae |
| Naja n. kaouthia | Family Elapidae |
| Vipera russellii | Family Viperidae |
| Oxyuranus scutellatus | Family Elapidae |
| Sea snake | Family Hydrolidae |

In order to measure the inhibition of toxicity, mice were injected with a predetermined lethal dose of the respective venoms in 0.1 ml volume intraperitoneally. Immediately, the control mice were injected with 0.5 ml 0.05M phosphate buffer saline (PBS) and the experimental with same volume of opossum or mongoose serum. For each experimental category, three (3) mice were used. The results are shown in Table I.

TABLE I

NEUTRALIZATION OF LETHAL EFFECTS OF SNAKE VENOMS BY OPOSSUM SERUM IN MICE

| | Death/Survival | |
|---|---|---|
| Venom | Opossum Serum | Control |
| Crotalus adamanteus | 0/3 | 3/0 |
| Crotalus atrox | 0/3 | 3/0 |
| Naja n. atra | 0/3 | 3/0 |
| Naja n. kaouthia | 0/3 | 3/0 |
| Vipera russellii | 0/3 | 3/0 |
| Oxyuranus s. scutellatus | 0/3 | 3/0 |
| Sea snake | 0/3 | 3/0 |

The results of Table I clearly show that opossum serum is rendering protection against lethal doses of various snake venoms from all families of poisonous snakes. The mice in controls died within 24 hours. As little as 0.5 ml of opossum serum is adequate to cause neutralization and render protection from the envenomation which otherwise would be lethal.

Opossum and mongoose sera were fractionated into immunoglobulin and albumin components by saturated ammonium sulfate treatment. The precipitated immunoglobulin component was dissolved in 0.05 M PBS to the starting volume of the serum. After dialysis, both albumin and immunoglobulin components were tested versus lethal doses of various snake venoms. The mice were injected with predetermined lethal doses of snake venoms followed by inoculation with 0.5 ml of albumin or immunoglobulin components. The results are presented in Table II.

TABLE II

NEUTRALIZATION OF LETHAL EFFECTS OF SNAKE VENOMS IN MICE BY OPOSSUM SERUM ALBUMIN COMPONENT

| | Death/Survival | |
|---|---|---|
| Venom | Albumin Component | Immunoglobulin component |
| C. atrox | 0/3 | 3/0 |
| N. n. kaouthia | 0/3 | 3/0 |
| V. russellii | 0/3 | 3/0 |

The results of the Table II clearly show that the protective factor resides in the albumin component of the opossum serum for the venoms of C. atrox, N. n. kaouthia and V. russellii. Thus, the neutralization of the toxic effects of venoms is not due to antigen antibody reaction.

Figure 1:
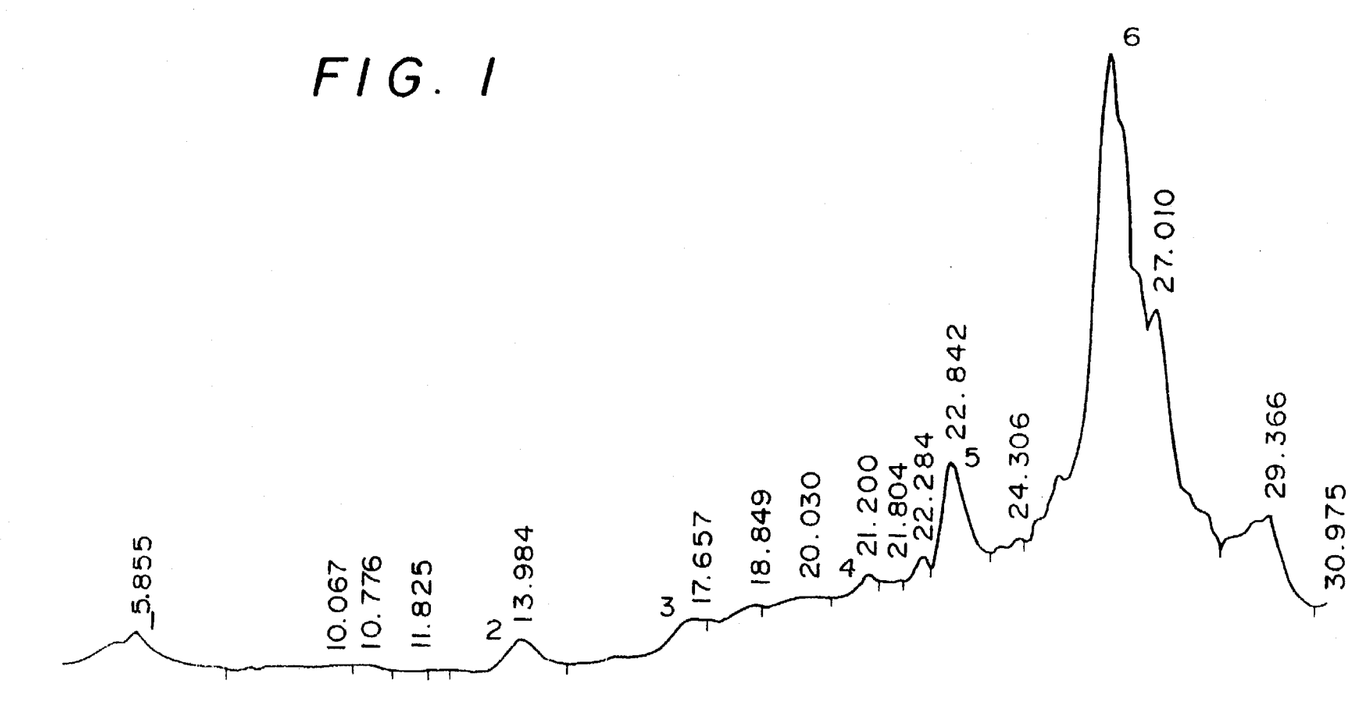

Opossum serum was fractionated on a liquid phase fractionating system. Specifically, using a high pressure liquid chromatography (HPLC), from Toso Co. Japan and anion exchange column (Type PL-SAX Q1125, with 10µparticles, 1000 Å pores and column dimensions 150×10 mm) from Polymer Laboratories UK, maintained at 20 ° C. temperature. Approximately 25 mg of serum protein was loaded into the column to fractionate. The elution was accomplished with gradient Trizma-HCl buffer having pH 7.4 and molarity gradient in the range 0.01M to 1.0 M. Nine different fractions were obtained which were individually pooled from several HPLC runs (Drawing no. 1). All fractions were dialyzed and concentrated using Spectrum dialysis apparatus. The protein concentration for each fraction was measured on spectrophotometer using protein assay kit from Bio-Rad company. Each fraction was adjusted to 1 mg/ml concentration of the protein content. Each fraction was mixed with an equal volume lethal dose of venom from C. atrox. In this case, 100 µg of the protein from each fraction was tested versus a predetermined lethal dose of C. atrox venom. Results are shown in Table III.

TABLE III

IDENTIFICATION OF VENOM NEUTRALIZING FACTOR FROM OPOSSUM SERUM

| Fraction # | Death/Survival |
|---|---|
| 1 | 3/0 |
| 2 | 3/0 |
| 3 | 3/0 |
| 4 | 3/0 |
| 5 | 3/0 |
| 6 | 0/3 |
| 7 | 3/0 |
| 8 | 3/0 |
| 9 | 3/0 |

The results of Table III show that the LTNF resides in fraction number 6 of the nine different fractions for C. atrox venom.

One hundred micrograms of purified fraction no. 6, which is the LTNF, LTNF-n, was mixed with an equal volume of the predetermined lethal doses of snake venoms to inject mice. The results are presented in Table IV.

TABLE IV

NEUTRALIZATION EFFECT OF FRACTION 6 OF OPOSSUM SERUM

| | Death/Survival | |
|---|---|---|
| Venoms | Fraction 6 | Control |
| C. atrox | 0/3 | 3/0 |
| Vipera russellii | 0/3 | 3/0 |
| N. n. kaouthia | 0/3 | 3/0 |
| O. s. scutellatus | 0/3 | 3/0 |
| Sea snake | 0/3 | 3/0 |

Figure 2:
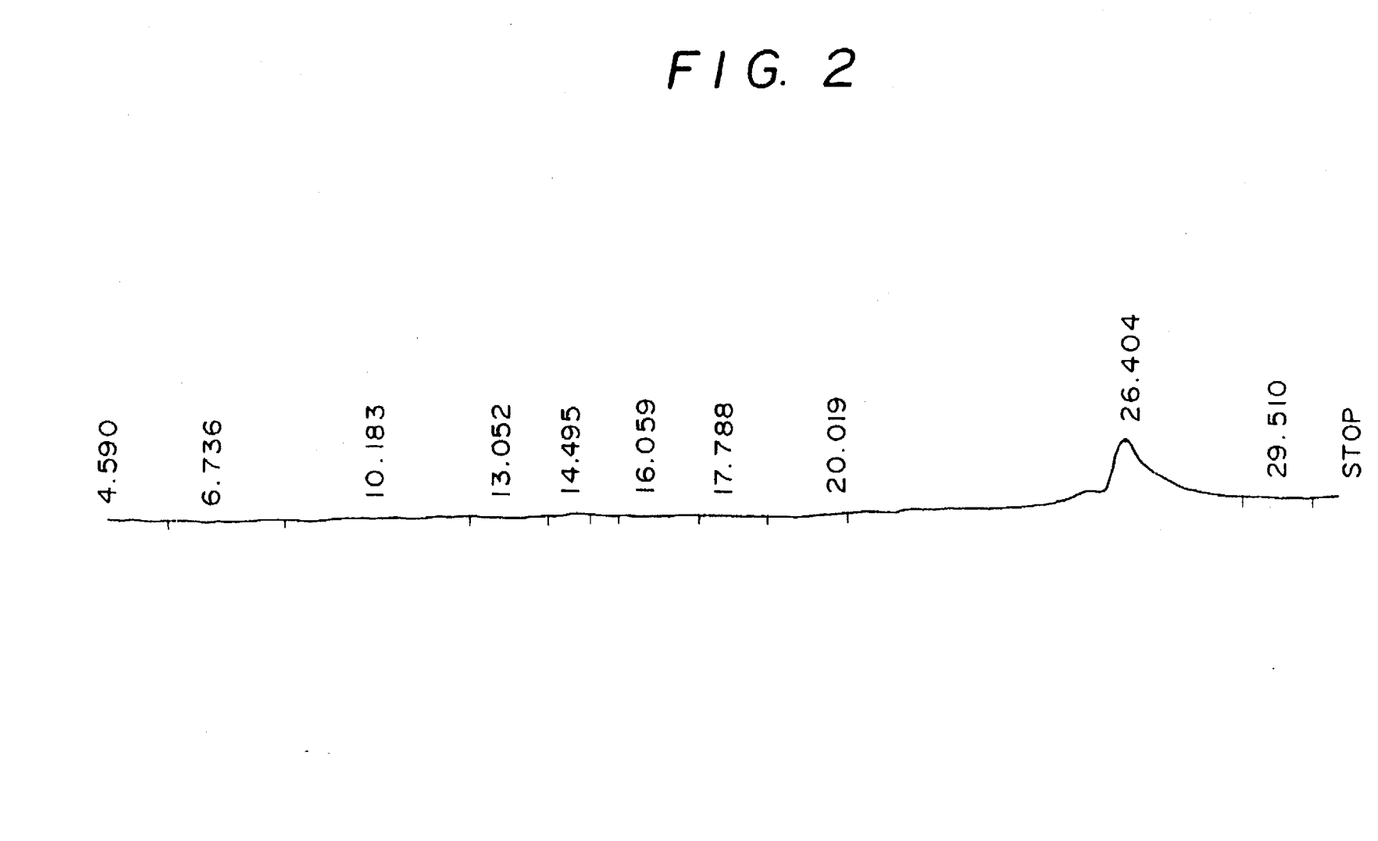
Figure 3:
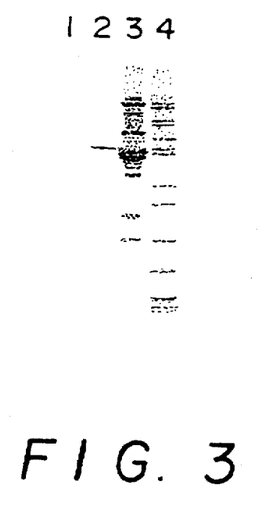

The fraction 6 is the LTNF-n showing ability to neutralize the toxic lethal effects of venoms of snakes from the major families. The fraction number six was concentrated and rerun on the HPLC under identical conditions of temperature, gradient buffer, etc. and it yielded one peak (Drawing no. 2). The material from this single peak was partially sequenced for its first fifteen amino acids of the N-terminal. Furthermore, a peptide for those fifteen amino acids, LTNF-15, was synthesized. The sequenced amino acids of N-terminal were identified as SEQ ID No: 1. Another peptide for the first 10 amino acids, LTNF-10, was synthesized, with the sequence being identified in SEQ ID No: 2. The molecular weight of LTNF-n was determined by gel electrophoresis. The molecular weight of LTNF-n was revealed to be approximately 68,000 daltons corresponding to the albumin component of the opossum serum. The molecular weight of LTNF-15 is less than 6,000 daltons (Drawing no. 3). LTNF-15 has a calculated molecular weight of 1,989. LTNF-10 has a calculated molecular weight of 1,242. LTNF-5 has a calculated molecular weight of 647.

The synthesized LTNF-15 was tested with the venoms as documented in Table V. Mice were divided into three groups. Mice in groups I & II were injected with lethal doses of respective venoms. Immediately, the mice in group I were injected with 0.5 ml of PBS, while those in group II were injected with 500 µg of LTNF-15 in 0.5 ml. Mice in group III were injected with 500 µg of LTNF-15 and after 30 minutes they were given lethal doses of respective venoms. The results are presented in Table V.

TABLE V

NEUTRALIZATION EFFECT OF LTNF-15

| | Death/Survival | | |
|---|---|---|---|
| Venoms | Group I (PBS Control) | Group II (LTNF Immediately) | Group III (LTNF ½ hr before) |
| C. atrox | 3/0 | 0/3 | 0/3 |
| N. n. kaouthia | 3/0 | 0/3 | 0/3 |
| V. russellii | 3/0 | 0/3 | 0/3 |
| O. s. scutellatus | 3/0 | 0/3 | 0/3 |
| Sea snake | 3/0 | 0/3 | 0/3 |

The results of Table V clearly show the strong antilethal activity of LTNF-15, similar to the LTNF-n, which is identified in opossum serum. The lack of antigenic relationship between snake venom and opossum serum or LTNF, indicates that its activity is immunoglobulin independent. Therefore, the activity of LTNF-s, which is similar to the LTNF-n, may extend to other toxins, viruses, allergens, etc. The antilethal activity of LTNF-s was exhibited when it was administered ½ hour before the toxin injection, therefore, LTNF-s can be used as a preventive measure, especially for snake handlers, etc.

Table VI sets forth data showing the results of further testing of the invention. In the experiment reflected by Table VI, six mice per venom or toxin were injected with a lethal dose of the venom or toxin intraperitoneally. 3 mice were given 100 µg of lethal toxin neutralizing factor (LTNF) in 0.5 ml phosphate buffer saline (PBS) and 3 were given 0.5 ml of PBS alone.

TABLE VI

NEUTRALIZING EFFECTS OF LTNF ON VENOMS

| Venoms | Death/Survival | |
|---|---|---|
| | LTNF | PBS |
| C. atrox | 0/3 | 3/0 |
| Vipera russellii | 0/3 | 3/0 |
| N. n. kaouthia | 0/3 | 3/0 |
| O. s. scutellatus | 0/3 | 3/0 |
| Scorpion A. austrailis | 0/3 | 3/0 |

The results show that LTNF neutralizes the lethal toxic effects of venoms belonging to the major snake families and scorpion venom.

For use with human victims of envenomation it is expected that at least one 1 mg of LTNF, such as in the range of 1 to 500 mg, should be administered as soon as possible after the envenomation occurs. The administration route can be oral, intranasal or intravenous, for example. For oral administration, LTNF-s is preferred, such as LTNF-15 or LTNF-10. Most preferably, an LTNF-s with the minimum number of amino acids required for forming the active site would be used, for most rapid absorption from the stomach. For intranasal use, a dose of 0.5 ml PBS containing LTNF at a concentration 2000 μg/ml would be expected to provide a beneficial result. For intravenous application a dose of 10 ml PBS containing LTNF at a concentration 100 μg/ml would be expected to provide a beneficial result.

Table VII sets forth additional data showing the results of testing the invention. In the experiment reflected by Table VII, six mice were injected with a lethal dose of venom or toxin intraperitoneally. 3 mice were given 100 μg of LTNF in 0.5 ml PBS and 3 were given 0.5 ml of PBS alone.

TABLE VII

NEUTRALIZING EFFECTS OF LTNF ON TOXINS

| | Death/Survival | |
|---|---|---|
| Toxin | LTNF | PBS |
| Cobratoxin | 0/3 | 3/0 |
| Crotoxin | 0/3 | 3/0 |
| Phospholipase A2 | 0/3 | 3/0 |
| Taipoxin | 0/3 | 3/0 |
| Ricin | 0/3 | 3/0 |

The results of Table VII show that LTNF neutralizes the lethal toxic effects of various purified snake venom toxins and the plant derived toxin ricin.

As was described previously, the opossum whole serum exhibits the property of neutralizing the lethality of venoms from major families of poisonous snakes. Because the neutralizing activity of opossum serum resides in the albumin component of the opossum serum, this neutralizing activity is not due to the antigen antibody reaction.

In the present invention, opossum serum was fractionated by high pressure liquid chromatography using an anion exchange column. The procedure yielded nine different fractions. The lethal neutralizing factor was found in fraction number six (Drawing no. 1). This fraction showed the neutralization of snake venoms. Fraction 6 was concentrated and fractionated a second time on HPLC under identical conditions. The purified product gave a single peak in the HPLC profile (Drawing no. 2). The molecular weight of the purified material was 68 kDa as revealed by gel electrophoresis (Drawing no. 3).

One hundred micrograms of LTNF-n neutralized the lethal toxicity of a variety of venoms. The LTNF-n exhibits the sequence for its first fifteen amino acids as SEQ ID No: 1. The known sequence of the fifteen amino acids of LTNF-n was synthesized as a short peptide. Five hundred micrograms of LTNF-15 is capable of neutralizing lethal doses of venoms from snakes from major families. Moreover, LTNF-s is immunogenic, since mice immunized with it were able to produce specific antibodies, which reacted with both LTNF-N and LTNF-s, thus proving its biological potency. The use of LTNF-n and LTNF-s can be expected to be useful as treatment for sepsis, allergies and other nonspecific disorders caused by the environment and as a preventive measure before possible exposure to various toxins.

The LTNF-n can be isolated from other species of opossums such as *Didelphis marsupialis, Philander opossum,* and *Lutreolina crassicaudata* and other animals like mongoose and meerkat.

The application of LTNF-n or LTNF-s, as treatment for snakebite, overcomes the problem of hypersensitivity occurring from the horse-derived antivenom.

LTNF-n is a non immunological component of opossum serum. Its molecular weight does not match any type of immunoglobulin. LTNF-n is an albumin, or is closely associated with, the albumin component of opossum serum. LTNF-15 is all of the first fifteen amino acids of LTNF-n. LTNF-10 is all of the first ten amino acids of LTNF-n.

The neutralizing activity of LTNF-n and LTNF-s is not due to the antigen antibody reaction. LTNF-n and LTNF-s do not show binding affinity to venoms, or toxins, in immunological tests such as immunopreciptin and Enzyme linked immunosorption (ELISA) tests. However, antisera versus LTNF-n, LTNF-15 and LTNF-10 elicit binding affinity to venoms, as well as toxins, by in vitro ELISA tests. Furthermore, these venoms and their lethal toxins are neutralized in vivo by LTNF-n, as well as LTNF-15 and LTNF-10.

Immunization of Mice

Adult Balb/C mice were immunized using LTNF-n, -15 and -10 as antigens, for the production of antibodies. The concentration of each antigen was 100 μg/ml, and 10 μg was given per mouse, three time, two weeks apart. The first dose consisted of antigen mixed with equal volume of Freund's complete adjuvant and 0.2 ml was injected in foot pads. The remaining two doses the antigen was mixed with equal volume of Freund's incomplete adjuvant and 0.2 ml was injected intramuscularly in thighs. Two weeks after the completion of the immunization process the mice were bled through the ophthalmic vein. The sera were separated and tested for binding affinity to various antigens, venoms and toxins, etc. by ELISA.

ELISA Test

A microtiter plate having 96 wells was used to run ELISA test by the standard technique. The antigens were diluted in 0.05 M PBS to yield 10 μg/ml and the wells were coated with 100 μl per well. After 24 hrs at room temperature (RT) the wells were washed three times with PBS. The wells were blocked by adding 250 μl/well of 3% gel for one hour at RT, after which the wells were washed three times with PBS.

The wells were then treated with serial two fold dilutions an antisera 100 µl/well with appropriate positive and negative controls. The reaction between the antigen and the antibody was allowed to take place at 37° C. for 2 hrs. The wells were washed three times with PBS and then reacted with anti-mouse IgG peroxidase conjugate (Sigma) made in goat, each well receiving 100 µl, and the plate was incubated at 37° C. for 1 hr. After which the plate was washed three times with PBS and then o-phenylenediamine Dihydrochloride-OPD (Sigma) was added to develop color reaction at RT. The titers of the antibodies were recorded after 30 minutes at RT. The results are shown in Table VIII.

TABLE VIII

Binding Affinity of Venoms and Toxins to Anti LTNF-n and LTNF-s by ELISA

| Antigen | ELISA Antibody Titer | | |
|---|---|---|---|
| | LTNF-n | LTNF-15 | LTNF-10 |
| LTNF-n | 12800 | 12800 | 12800 |
| LTNF-15 | 800 | 1600 | 600 |
| LTNF-10 | 800 | 400 | 1600 |
| C. atrox venom | 600 | 600 | 800 |
| N. n. Kaouthia venom | 800 | 400 | 400 |
| R. viper venom | 3200 | 1600 | 1600 |
| O scutellatus venom | 300 | 600 | 600 |
| Scorpion venom | 600 | 600 | 800 |
| Bee venom | 7200 | 1600 | 1600 |
| Ricin | 600 | 300 | 800 |
| Cobratoxin | 1600 | 1600 | 3200 |
| Phospholipase (PhLA2) toxin | 800 | 800 | 1600 |
| Taipoxin | 1600 | 1600 | 3200 |

Table VIII shows that antibodies versus LTNF-n and synthetics with 15 and 10 amino acids reacted more or less similarly with venoms and toxins. Such binding did not occur when non toxic proteins, such as fetal bovine serum (FBS) or bovine serum albumin (BSA) were tested. The results of binding affinity towards venoms and toxins by LTNF-n and LTNF-s constructed out of 15 and 10 amino acids illustrate that the sequence of only 10 amino acids contains an active site. The toxins show binding affinity to the anti-sera versus LTNF-n or LTNF-s by ELISA in vitro system, their lethality is neutralized by their antigens when tested in mice in vivo system. The mechanism for neutralization of venoms and toxins by the LTNFs is a protein—protein interaction, which is not fully understood. However, it is not due to immunological antigen - antibody reaction.

From these studies it is clear that the activity of LTNF-n resides in the first ten amino acids, or perhaps even less. It is known that the first five amino acids from the N-terminal of the antihemorrhagic factors isolated from: *Didelphis marsupilis* (which is closely related to *Didelphis virginia*), *Philander opossum* and *Lutreolina crassicaudatis* are identical. The first five amino acids from the N-terminal of LTNF-n from *Didelphis virginiana* is also identical and therefor the 5-amino acid sequence set forth in Sequence ID No. 3 is a highly conserved domain. Thus, a peptide consisting of the five amino acids L K A M and D, can be as active as the LTNF-10, or may be even more, as our results show that LTNF-10 is more active than LTNF-15 on a mass basis.

LTNF-n is a large molecule must be administered intravenously (IV), as a treatment for snake, scorpion or insect bites. LTNF-10 has a molecular weight of about 1,242 daltons and can be given orally because its molecular weight is low enough to be readily absorbed into blood directly from the stomach. A synthetic peptide out of five amino acids would have a molecular weight of only about 647 and can be even better from the point of bioavailability and economics.

Additional data

LTNF has been applied topically to a human to treat a bee sting which had become swollen and stiff. The itching stopped immediately and the inflammation and stiffness were reduced soon thereafter.

LTNF was applied topically to a human to treat a skin allergy and provided immediate relief from the itching caused by the allergy.

LTNF was applied topically to the hands of a human suffering from arthritis. The pain was relieved shortly after the application of the LTNF.

A person suffering from asthma took LTNF by nasal insufflation and experienced relief with sinus clearance in a short time. Another person with a long term history of being unable to breathe through their nose took LTNF by nasal insufflation and experienced relief in three days.

From these observations, it appears that LTNF is a potent anti-histamine, and may find use in general where such activity is desired.

To investigate the effect of LTNF on the toxic effect of botulinum toxin derived from *Clostridium botulinum* bacteria, six mice were injected with botulinum toxin intraperitoneally. 3 mice were given 100 µg of LTNF in 0.5ml PBS and 3 were given 0.5ml of PBS alone. The 3 mice injected with the LTNF showed no signs of illness while the 3 injected with PBS alone became very sick. It was not reasonably possible to get a lethal effect from the *botulinum* toxin used in the experiment.

The foregoing disclosure and description of the invention is illustrative and explanatory thereof. Various changes in the steps of the described method, or the details of the claim composition, can be made within the scope of the appended claims without departing from the true spirit of the invention.

What is claimed is:

1. A peptide having a molecular weight in the range of 250 to 2,500 g/mole and comprising at least a 3 amino acid portion of the sequence set forth in Sequence ID. No. 1.

2. The peptide of claim 1 comprising at least a 5 amino acid portion of the sequence set forth in Sequence ID. No. 1.

3. The peptide of claim 1 having a molecular weight in the range of 500 to 2,000 g/mole.

4. The peptide of claim 3 comprising at least a 5 amino acid portion of the sequence from the N-terminal of the sequence set forth Sequence ID No. 1.

5. The peptide of claim 4 having the sequence set forth in Sequence ID No. 3.

6. The peptide of claim 3 comprising at least a 7 amino acid portion of the sequence from the N-terminal of the sequence set forth in Sequence ID No. 1.

7. The peptide of claim 6 having the sequence set forth in Sequence ID No. 2.

8. The peptide of claim 6 having the sequence set forth in Sequence ID No. 1.

9. A method for treating a victim of envenomation from a poisonous snake, said method comprising administering to said victim a peptide having a molecular weight in the range of 250 to 2,500 g/mole and comprising at least a 3 amino acid portion of the sequence set forth in Sequence ID. No. 1 by a route and in an amount which is effective to neutralize at least one effect of the envenomation.

10. The method of claim 9 wherein the peptide comprises at least a 5 amino acid portion of the sequence from the N-terminal of the sequence set forth Sequence ID No. 1.

11. The method of claim 10 wherein at least one milligram of the peptide is administered to the victim.

12. The method of claim 11 wherein in the range of 1 to 500 milligrams of the peptide is administered intravenously to the victim.

13. The method of claim 11 wherein in the range of 1 to 500 milligrams of the peptide is administered orally to the victim.

14. A method for treating a victim of envenomation from a poisonous snake from the family of Elapidae, Viperidae or sea snake, said method comprising administering to said victim a protein having a molecular weight of about 68 kDa and an initial 15 amino acid sequence as set forth in Sequence ID. No. 1 by a route and in an amount which is effective to neutralize at least one effect of the envenomation.

15. The method of claim 14 wherein in the range of 1 to 500 milligrams of the protein is administered intravenously to the victim.

16. A method for treating a victim of a histamine reaction, said method comprising administering to said victim a peptide having a molecular weight in the range of 250 to 2,500 g/mole and comprising at least a 3 amino acid portion of the sequence set forth in Sequence ID. No. 1 by a route and in an amount which is effective to neutralize at least one effect of the histamine reaction.

17. The method of claim 16 wherein the peptide comprises at least a 5 amino acid portion of the sequence from the N-terminal of the sequence set forth Sequence ID No. 1.

18. The method of claim 17 wherein a solution containing the peptide is applied topically to an area affected by the histamine reaction.

19. The method of claim 17 wherein the peptide is orally administered to the victim.

20. The method of claim 17 wherein the peptide is administered to the victim by nasal insufflation.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 15
        ( B ) TYPE: AMINO ACID (C) STRANDEDNESS: SINGLE
(D) TOPOLOGY: LINEAR (ii) MOLECULE TYPE: PROTEIN IN SEQ ID NO: 1

(iii) HYPOTHETICAL: NO (iv) ANTI-SENSE: NO (v) FRAGMENT TYPE: N (vi) ORIGINAL SOURCE: OPOSSUM SERA: SEQ ID NO: 1:
    (A) ORGANISM: DIDELPHIS VIRGINIANA
    (B) STRAIN: WILD
    (C) INDIVIDUAL ISOLATE: TEXAS WILD
    (D) DEVELOPMENTAL STAGE: ADULT
    (E) HAPLOTYPE:
    (F) TISSUE TYPE: BLOOD
    (G) CELL TYPE:
    (H) CELL LINE:
    (I) ORGANELLE:

(vii) IMMEDIATE SOURCE: OPOSSUM SERA SEQ ID NO: 1:
    (A) LIBRARY:
    (B) CLONE:

(viii) PUBLICATION INFORMATION:
    (A) AUTHORS: JONAS PERALES, ET AL.
    (B) TITLE: ANTI-SNAKE VENOM FORM DIDELPHIDAE
    (C) JOURNAL: INTERNATIONAL SOCIETY ON
        TOXICOLOGY
    (D) VOLUME: 10TH WORLD CONGRESS ON ANIMAL
        PLANT AND MICROBIAL TOXINS 3-8 NOV 1991, SINGAPORE
    (E) ISSUE: PROGRAMME AND ABSTRACTS
    (F) PAGES: 104
    (G) DATE: 3-8 NOV 1991

(ix) SEQUENCE DESCRIPTION: SEQ ID NO: 1:

```
Leu Lys Ala Met Asp Pro Thr Pro Pro Leu
1               5                   10

Trp Ile Lys Thr Glu
                15
```

(2) INFORMATION FOR SEQ ID NO: 2:

(i) SEQUENCE CHARACTERISTICS:
    (A) LENGTH: 10
    (B) TYPE: AMINO ACID
    (C) STRANDEDNESS: SINGLE
    (D) TOPOLOGY: LINEAR (ii) MOLECULE TYPE: PEPTIDE IN SEQ ID NO: 2

(iii) HYPOTHETICAL: NO (iv) ANTI-SENSE: NO (v) FRAGMENT TYPE: N (vi) ORIGINAL SOURCE: SYNTHETIC (vii) SEQUENCE DESCRIPTION: SEQ ID NO: 2:

```
Leu Lys Ala Met Asp Pro Thr Pro Pro Leu
1               5                   10
```

(2) INFORMATION FOR SEQ ID NO: 3:

(i) SEQUENCE CHARACTERISTICS:
    (A) LENGTH: 5
    (B) TYPE: AMINO ACID
    (C) STRANDEDNESS: SINGLE
    (D) TOPOLOGY: LINEAR (ii) MOLECULE TYPE: PEPTIDE IN SEQ ID NO: 3

(iii) HYPOTHETICAL: YES

(iv) ANTI-SENSE: NO

(v) FRAGMENT TYPE: N

(vi) ORIGINAL SOURCE: SYNTHETIC

(xiii) SEQUENCE DESCRIPTION: SEQ ID NO: 3:

Leu Lys Ala Met Asp
1               5